(12) United States Patent
Huntley et al.

(10) Patent No.: US 9,075,022 B2
(45) Date of Patent: Jul. 7, 2015

(54) SYNTHETIC ROPE, FIBER OPTIC CABLE AND METHOD FOR NON-DESTRUCTIVE TESTING THEREOF

(71) Applicant: Whitehill Manufacturing Corporation, Lima, PA (US)

(72) Inventors: Elizabeth W. Huntley, Chadds Ford, PA (US); Mark B. Huntley, Chadds Ford, PA (US); A. Simeon Whitehill, West Chester, PA (US)

(73) Assignee: WHITEHILL MANUFACTURING CORPORATION, Lima, PA (US)

( * ) Notice: Subject to any disclaimer, the term of this patent is extended or adjusted under 35 U.S.C. 154(b) by 133 days.

(21) Appl. No.: 13/838,509

(22) Filed: Mar. 15, 2013

(65) Prior Publication Data

US 2014/0266169 A1  Sep. 18, 2014

(51) Int. Cl.
*G01R 33/14* (2006.01)
*G01N 27/82* (2006.01)
*G01N 27/90* (2006.01)
*G02B 6/44* (2006.01)
*G01V 1/00* (2006.01)
(Continued)

(52) U.S. Cl.
CPC ............... *G01N 27/82* (2013.01); *G01N 27/90* (2013.01); *G02B 6/4401* (2013.01); *G01V 1/00* (2013.01); *G01V 2200/00* (2013.01); *G01D 1/00* (2013.01); *D07B 1/145* (2013.01); *D07B 2301/555* (2013.01); *D07B 1/025* (2013.01); *D07B 1/147* (2013.01); *D07B 2201/2043* (2013.01)

(58) Field of Classification Search
CPC . G01V 1/00; G01V 2001/00; G01V 2200/00; G01V 2210/00; B82Y 5/00; G01D 1/00; G01R 1/00; G01R 2019/00; D01F 1/00

USPC .......................................................... 324/222
See application file for complete search history.

(56) References Cited

U.S. PATENT DOCUMENTS 4,022,057 A  *  5/1977  Bachman et al. ............... 73/847
4,158,962 A        6/1979  Conoval
(Continued)

FOREIGN PATENT DOCUMENTS

DE  20 2010 013 519 U1   12/2010
EP         0 731 209 A1    9/1996
(Continued)

OTHER PUBLICATIONS

International Search Report issued in International Patent Application No. PCT/US2014/016884 dated Apr. 30, 2014.
(Continued)

*Primary Examiner* — Huy Q Phan
*Assistant Examiner* — Temilade S Rhodes-Vivour
(74) *Attorney, Agent, or Firm* — Oliff PLC

(57) ABSTRACT

A non-destructive test method for evaluating a synthetic rope made of strength member elements includes: treating at least one strength member element to be detectable by a magnetic NDT device, incorporating the at least one treated strength member element into the rope, scanning the synthetic rope with the magnetic NDT device, and obtaining magnetic flux leakage or eddy current output data from the magnetic NDT device, wherein the output data relates to a condition of the synthetic rope. A synthetic rope or cable is thereby made to be capable of being inspected by a magnetic flux leakage or eddy current non-destructive test (NDT) method.

16 Claims, 1 Drawing Sheet

(51) Int. Cl.
*G01D 1/00* (2006.01)
*D07B 1/14* (2006.01)
*D07B 1/02* (2006.01)

(56) References Cited

U.S. PATENT DOCUMENTS

| | | | |
|---|---|---|---|
| 4,979,125 A | 12/1990 | Kwun et al. | |
| 5,305,411 A * | 4/1994 | Arroyo | 385/109 |
| 5,541,522 A * | 7/1996 | Rosen et al. | 324/642 |
| 5,821,430 A | 10/1998 | Kwun et al. | |
| 5,834,942 A | 11/1998 | De Angelis | |
| 5,992,574 A | 11/1999 | Olsen et al. | |
| 6,289,742 B1 | 9/2001 | De Angelis | |
| 6,392,551 B2 | 5/2002 | De Angelis | |
| 6,608,487 B2 | 8/2003 | De Angelis | |
| 6,886,666 B2 * | 5/2005 | Stucky et al. | 187/393 |
| 7,123,030 B2 | 10/2006 | Robar et al. | |
| 7,277,822 B2 | 10/2007 | Blemel | |
| 7,326,139 B2 | 2/2008 | Eichhorn et al. | |
| 7,357,028 B2 * | 4/2008 | Kim | 73/627 |
| 7,516,605 B2 | 4/2009 | Goldwater et al. | |
| 8,069,011 B2 * | 11/2011 | Liu et al. | 702/181 |
| 8,358,126 B2 * | 1/2013 | Light et al. | 324/240 |
| 8,360,208 B2 | 1/2013 | De Angelis | |
| 2001/0030608 A1 | 10/2001 | De Angelis | |
| 2003/0062225 A1 | 4/2003 | Stucky et al. | |
| 2004/0225213 A1 * | 11/2004 | Wang et al. | 600/421 |
| 2010/0148766 A1 * | 6/2010 | Weischedel | 324/238 |
| 2011/0171749 A1 * | 7/2011 | Alocilja et al. | 436/501 |
| 2011/0259677 A1 | 10/2011 | Dudde et al. | |
| 2012/0053852 A1 * | 3/2012 | Padilla et al. | 702/34 |

FOREIGN PATENT DOCUMENTS

| | | | | |
|---|---|---|---|---|
| GB | 1228590 | * | 6/1967 | G01R 33/18 |
| GB | 2 152 088 A | | 7/1985 | |
| IN | 206767 B | | 12/1999 | |
| JP | A-2001-302135 | | 10/2001 | |
| WO | WO 99/53282 A1 | | 10/1999 | |

OTHER PUBLICATIONS

Written Opinion of the International Searching Authority issued in International Patent Application No. PCT/US2014/016884 dated Apr. 30, 2014.

Xu et al. "A Magnetic Flux Leakage and Magnetostrictive Guided Wave Hybrid Transducer for Detecting Bridge Cables," *Sensors*, vol. 12, pp. 518-533, 2012 (http://mdpi.com/1424-8220/12/1/518/htm).

* cited by examiner

SYNTHETIC ROPE, FIBER OPTIC CABLE AND METHOD FOR NON-DESTRUCTIVE TESTING THEREOF

BACKGROUND

Wire rope, for example made up of steel elements, is used extensively in critical applications, such as in mine hoists or cranes. As a result of use, the strength properties of the wire rope can deteriorate. In some applications, for example, when wire rope is used as a mooring line, the rope can suffer from tension-tension fatigue. That is, the rope is subjected to a cyclic increase and decrease of tension, which detrimentally affects its properties. In other applications, for example, where wire rope is used over pulleys, the wire rope can suffer from bending fatigue in use. That is, the properties of the wire rope deteriorate when the wire rope is subjected repeatedly to bending.

One of the key concerns of a wire rope user is to determine when the wire rope should be replaced. Replacing a wire rope entails substantial costs and effort. These include not only the cost of the new wire rope and labor associated with its replacement, but also the costs associated with down-time of the unit in which the wire rope is used. Therefore, it is undesirable to replace a wire rope too soon, that is, substantially before the end of its useable lifetime. On the other hand, the situation that a wire rope breaks or otherwise fails is unacceptable, and needs to be prevented.

Therefore, within the wire rope field methods have been developed to test the properties of the wire rope while it is in use to allow the wire rope user to determine when to retire a given segment or set of wire ropes. Testing the properties of a wire rope while it is in use may be accomplished by non-destructive testing (NDT) methods.

A first non-destructive testing method that may be used for wire rope evaluation is magnetic field testing, wherein the wire rope to be tested is brought into a magnetic field, and the presence of defects in the wire rope is detected through areas of flux leakage. A further method is eddy current testing wherein an alternating electrical current is passed through a coil producing a magnetic field. When the coil is placed near a conductive material, the changing magnetic field induces current flow in the material. These currents travel in closed loops and are known as eddy currents. Eddy currents produce their own magnetic field that can be measured and used to determine the presence of flaws in the wire rope. In general, NDT methods monitor for changes in the wire ropes shape and geometry over time, as well as for localized breaks within the elements of the wire rope, all of which are indicative of wear and damage to the wire rope. The NDT methods can indicate when predetermined damage thresholds are passed such that the wire rope requires replacement.

In addition to the above, wire ropes are also monitored through visual inspections of the outer strands to identify the number and density of broken wires within the rope.

SUMMARY

Synthetic ropes are in principle very attractive to replace wire ropes in numerous applications because they have a number of advantages over wire ropes including: higher strength to weight ratios, increased corrosion resistance, better fatigue life, and lower maintenance requirements. However, for synthetic rope to be used in high risk applications, the availability of accurate and reliable methods for testing the rope's properties and condition in use is required. While the methods specified above have value in evaluating wire ropes, they are not presently applicable to synthetic ropes, because the methods rely on the magnetic and electrically conductive properties of the wire rope, and synthetic ropes do not have magnetic or conductive properties.

The evolution over time of the general shape and geometry of a synthetic rope in use is difficult to monitor for several reasons, rendering it very difficult to monitor the condition of synthetic ropes. Synthetic materials such as aramid, PBO, HMPE, LCP, nylon, glass, polyester, and polypropylene are non-metallic and non-conductive, and therefore cannot be monitored with magnetic NDT devices typically used to monitor wire ropes. The problem of synthetic rope evaluation is often further exacerbated because a non-load-bearing cover is often applied to the rope structure to protect the strength-member fibers of the synthetic rope from damage and/or ultra-violet exposure. This cover obscures the strength-member fibers from visual inspection.

Moreover, even if the strength-member fibers are exposed for visible inspection, the fibers are often so small that it is difficult and impractical to accurately quantify an amount and/or density of broken or otherwise degraded fibers.

What is still desired is a useful and reliable method to allow synthetic ropes to be monitored during use to determine the extent of damage to the synthetic rope from the use.

Thus, according to one embodiment, a non-destructive test method for evaluating a synthetic rope comprised of strength-member fibers is provided. The method comprises: treating at least one synthetic material strength member element of the rope to be detectable by a magnetic NDT device, incorporating the at least one treated strength member element into the rope, scanning the rope with the magnetic NDT device, and obtaining magnetic flux leakage or eddy current output data from the scanning, wherein the output data relates to a condition of the rope.

According to another embodiment, a synthetic rope is provided comprising synthetic material strength member elements, wherein at least one synthetic material strength member element is a treated strength member element, and the treated strength member element renders the synthetic rope capable of being inspected by a magnetic non-destructive test (NDT) method.

The above-discussed principles can be similarly applied to other fields as well, and thus also described in another embodiment is a fiber optic cable comprising at least one optical transmission element and at least one treated element, wherein the at least one treated element renders the fiber optic cable capable of being inspected by a magnetic or electromagnetic non-destructive test method.

DETAILED DESCRIPTION

Figure 1:
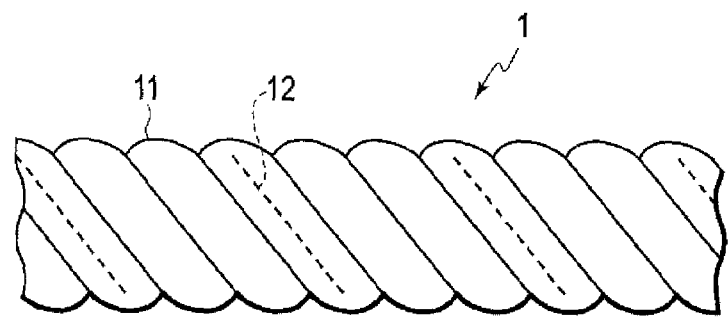
FIG. 1 is a view of a synthetic rope with a treated synthetic material strength member element embedded therein according to one embodiment.

In the present specification, the term "rope" is used to denote a final rope product. The term "filament" is used to refer to small individual elements in the rope, for example, the polymer fibers making up the rope. The term "fiber" is a plurality of filaments. The term "yarn" is used to refer to a longitudinal association of one or more fibers, associated together by any suitable means, for example by plying or twisting. The term "strand" is used to refer to one or more yarns which, together with other strands, are combined to form a structured rope. A "strength member element" of the rope as used herein thus refers to one or more of a filament, a fiber, a strand or a yarn to be incorporated into a rope.

A synthetic rope is, for example, a rope comprised of synthetic load-bearing strength member elements as opposed to wire elements, such as in steel ropes. The synthetic strength member elements are comprised of synthetic or non-metal materials such as, for example, aramid, meta-aramid (Nomex), polybenzoxazole (PBO), liquid crystal polymer (LCP, for example commercially known as Vectran), polytetrafluoroethylene (PTFE), high-modulus polyethylene, (HMPE), polyamide (such as, for example, nylon), polyester, polyethylene, glass, and polypropylene. Typically, the materials used for the strength member elements are formed into yarn bundles which are then formed into strands for use in the rope. A synthetic protective jacket is often applied around the individual strands or the entire rope structure. The strength member elements and jacketing materials of the synthetic rope derived from such materials are not detectable by NDT methods such as magnetic flux leakage or eddy current methods. Jackets are typically applied by braiding any one or combination of the synthetic materials listed above or by extrusion.

While embodiments herein refer to the synthetic elements being formed into a synthetic rope, one of ordinary skill will appreciate that the synthetic elements may also be incorporated to form cables, belts, cords, lines, and the like.

In one embodiment, aramid fibers are used, such as para-aramid fibers. Para-aramid is shorthand for para-oriented aromatic polyamides, which are condensation polymers of a para-oriented aromatic diamine and a para-oriented aromatic dicarboxylic acid halide. The aramids of which structures have a poly-para-oriented form or a form close thereto include aramids such as poly(paraphenyleneterephthalamide), poly(4,4'-benzanilide terephthalamide), poly(paraphenylene-4,4'-biphenylenedicarboxylic acid amide) and poly (paraphenylene-2,6-naphthalenedicarboxylic acid amide or copoly(para-phenylene/3,4'-dioxydiphenylene terephthalamide). Para-aramid is commercially available, for example under trade names such as Twaron®, Technora®, and Kevlar®.

In order to render the synthetic rope detectable by a magnetic or electro-magnetic NDT device (that is, a device that operates based upon electro-magnetic feedback from a material), one or more of the strength member elements of the rope are treated so as to be detectable by a magnetic NDT device. This may be done in any number of suitable ways, as discussed below. Simple incorporation of metal wires into the rope are excluded; where metal wires are used as the detectable portion of the rope, the metal fibers are used to treat the strength member elements, for example by wrapping a plurality of strength fiber elements to form a treated strength member strand or yarn, as further explained herein.

In embodiments, one or more strength member elements are treated by including an outer coating or cladding on the strength member elements, which coating or cladding is detectable by a magnetic NDT device (that is, detectable by NDT methods such as magnetic flux leakage or eddy current methods). The treated synthetic fiber is then used to make the synthetic rope. The synthetic rope may include all treated synthetic fibers, or it may include both treated strength member elements and untreated strength member elements.

The treated strength member elements may be synthetic fibers that are coated with a material detectable by NDT methods, for example, the treated synthetic fibers may have an NDT detectable material adhered, coated, cladded, dyed, or otherwise attached to the synthetic fibers. The NDT detectable material may be derived from, for example, a metallic material such as nickel, iron, cobalt, copper, or steel. The synthetic fibers may be treated by adding onto the synthetic fibers the coating or cladding material by any suitable method (s). Treated synthetic fibers may also be commercially obtained, for example such as Aracon® (a nickel clad aramid fiber) from Micro-Coax.

The treated synthetic fiber in this embodiment is thus comprised of a material to enable it to be detectable by a magnetic or electro-magnetic NDT device. The treated synthetic fiber may also be any magnetically detectable material such as, but not limited to, electro-conductive textiles, where a synthetic fiber is treated by methods such as coating, embedment, or cladding with a material that responds to electro-magnetism.

In an alternative embodiment, the elements may comprise optical transmission elements derived from, for example, glass fibers, such as in a fiber optic cable. The optical transmission elements are generally not detectable by magnetic NDT methods. A treated synthetic fiber or treated glass fiber as described above may be incorporated with the optical transmission elements, allowing the fiber optic cable to be detectable by magnetic NDT methods.

An example synthetic rope 1 of according to one embodiment is shown in FIG. 1. Although FIG. 1 shows the synthetic rope 1 being a 3-strand synthetic rope, the synthetic rope may be any of a variety of synthetic rope structures including, but not limited to, braided ropes such as 8-part or 12-part braids, double-braids, stranded ropes, such as 3-strand, 4-strand, 6-strand, 8-strand, multi-layer wire-lay and cross-laid constructions and twisted rope structures. The strength member elements could be exposed or covered with individual strand jackets or an overall jacket.

The synthetic rope 1 is made up of three separate strands 11 which together are combined to form the synthetic rope 1. Each strand 11 incorporates one or more yarns made up of a plurality of strength member elements. In the example 3-strand synthetic rope 1, one of the three strands 11 of the rope 1 includes a treated strength member element 12 embedded in the strand. Of course, this is merely exemplary for illustrative purposes, and the rope may include more than one treated strength member element in a strand, or may include treated strength member elements in more than one strand.

The treated strength member element 12 is formed integrally with a strand 11 of the synthetic rope 1, and desirably runs throughout the length of the strand 11 of the synthetic rope 1.

Where the synthetic rope will include both treated and untreated treated strength member elements, the treated strength member element is desirably selected based on its material properties in comparison with the material properties of the other untreated strength member elements used in the synthetic rope. In order to accurately and conservatively model the condition of the synthetic rope, the treated strength member elements may have a stiffness less than, higher than, or equal to a stiffness of the untreated strength member elements of the synthetic rope. The treated strength member elements may make up anywhere from as little as one treated synthetic fiber in the rope up to 100% by weight of the rope.

For example, the treated strength member elements of the rope may be comprised of a base material that has the same or substantially the same stress-strain characteristics, or modulus of elasticity, as the untreated strength member elements.

For example, when the untreated strength member elements comprise aramid fibers, the treated strength member elements may comprise aramid fibers with metallic cladding. In this example, because the treated strength member elements are of the same material as the strength member elements, an accurate representation of the condition of the strength member elements may be detected by an NDT device.

As another example, the treated strength member elements may have a stiffness higher than the untreated strength member elements. In this example, because the stiffness of the treated strength member elements is higher than the untreated strength member elements, the treated strength member elements will fail before the untreated strength member elements. Accordingly, the damage or breaks in the treated strength member elements may be detected by an NDT device.

As another example, the treated strength member elements may have a stiffness less than the untreated strength member elements. In this example, because the stiffness of the treated strength member elements are less than the untreated strength member elements, the treated strength member elements will retain sufficient elasticity to accurately model a geometry of the synthetic rope without sustaining damage or breaks.

It will also be appreciated that if multiple treated strength member elements are used in a synthetic rope, treated strength member elements having different material properties may be chosen. In this manner, treated strength member elements having a stiffness less than, higher than, or equal to the untreated strength member elements may be incorporated simultaneously into the synthetic rope.

The treated strength member element may be a treated synthetic fiber. The treated strength member element may also comprise a plurality of treated synthetic fibers wound into a yarn. Alternatively, the treated strength members may comprise a plurality of fibers wound into a yarn, and the yarn being treated as described above. Of course, treated synthetic fibers may be wound into a yarn with untreated strength member fibers, or the treated strength member fibers alone may be wound into a yarn. One or more strength member elements are then incorporated into at least one strand of the synthetic rope. When the above described treated strength member element(s) are used in an aramid rope, the treated strength member element(s) will have substantially the same performance properties as the untreated strength member elements of the synthetic rope. This is advantageous in that the changes detected in the treated strength member element(s) during use will directly correspond to changes that the untreated strength member elements have also undergone, such that an accurate picture of the overall condition of the rope can be obtained from inspection of the treated strength member elements.

In FIG. 1, the synthetic rope 1 is shown to have a single treated strength member element 12 in one strand 11 of a 3-strand synthetic rope 1. However, it is possible to incorporate multiple treated strength member elements into the strand 11, and to incorporate treated strength member elements into other or all strands 11 of the 3-strand rope 1. In addition, each and every fiber of the synthetic rope 1 could be coated or cladded with a metallic or otherwise magnetic material enabling all of the fibers of the synthetic rope 1 to be detectable by a magnetic NDT device. By increasing the number of treated strength member elements 12, the number of elements detectable by a magnetic NDT device increases. However, increasing the number of treated strength member elements 12 may also increase the overall cost of the synthetic rope 1.

In order to ensure that the structure of the synthetic rope is adequately represented, treated strength member elements may at least be dispersed throughout the rope structure in the various layers, positions, and directions. That is, if the synthetic rope has multiple layers, directions, and patterns, at least one treated strength member element is desirably embedded at least in each layer, direction, and pattern so that each of the separate sections/portions of the rope may be evaluated by the NDT method.

In embodiments where the treated strength member element is a coated or clad strength member fiber, the coating or cladding may continuously cover the entire length of the fiber.

It will be appreciated that the treated strength member element is not limited to being incorporated into strands of the synthetic rope. For example, in another embodiment, when the synthetic rope comprises a protective outer jacket, a treated strength member element is incorporated into the outer jacket. In a further embodiment, when the synthetic rope comprises protective strand jackets around separate strands in the synthetic rope, a treated strength member element is incorporated into one or more of the protective strand jackets. The treated strength member fiber incorporated into either an outer jacket or strand jacket may be of the same or of a different base material as the jacket.

Figure 2:
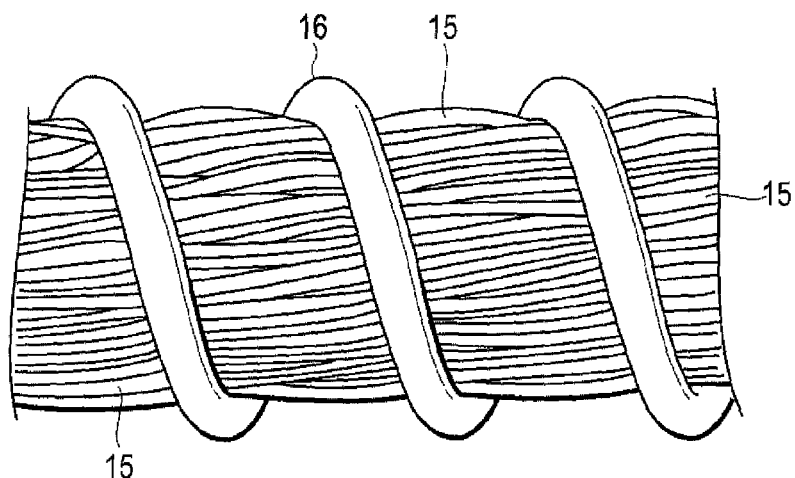
FIG. 2 is a view of a treated strength member element for incorporation into a synthetic rope according to one embodiment.

Another embodiment of a treated strength member fiber is shown in FIG. 2. In this embodiment, a plurality of strength member elements 15, such as synthetic fibers or yarns, are treated so as to be detectable by an electro-magnetic NDT device by wrapping a magnetically detectable element 16 around the strength member elements 15 to form a treated strength member element. The magnetically detectable element 16 wrapped around the strength member elements 15 may be, for example, a wire of any suitable magnetic material including metallic material such as nickel, iron, cobalt, or steel. As another example, the magnetically detectable element 16 may be one or more synthetic fibers treated with a magnetic material as described above. In the embodiment of FIG. 2, the strength member elements 15 may be a plurality of fibers, and the element 16 is wrapped there around to assist in the formation of the plurality of fibers into a treated strength member yarn.

The magnetically detectable element 16 may have strength properties that are the same or substantially the same as the plurality of strength member elements 15 it surrounds. The magnetically detectable element 16 may also have a stiffness that is the same or less than the strength member elements 15. For example, when the magnetically detectable element 16 is one or more synthetic fibers treated with a magnetic material, the synthetic fibers of the detectable element 16 and synthetic fibers of the strength member elements 15 may be derived from the same materials. Accordingly, the detectable element 16 would have the same or substantially the same strength properties as the strength member elements 15.

As another example, when the detectable element 16 is a wire, the wire may be chosen such that a stiffness of the wire is less than the stiffness of the strength member elements 15. For example, the wire may be tinsel wire or tinsel wire type structure with magnetic material.

In embodiments, it is further possible to treat several strength member elements with various separately distinguishable materials for more refined analysis. For example, strength member elements with one type of treatment may be on one layer of the rope structure and strength member elements with a different treatment may be located on another layer. By analyzing the unique response of the different treatments, the exact location and mode of failure may be more accurately determined.

In embodiments, it is further possible to provide treated strength member elements with varying degrees of twist. For example, low levels of twist would give the treated strength member element a relatively high stiffness and a propensity to break first or prematurely as an early warning indicator. As another example, higher levels of twist would give the strength member element a relatively low stiffness and a propensity to remain intact longer than the rest of the strength member elements. The low stiffness element would ensure that the lay length would continue to be accurately detectable as the rope deteriorated.

By embedding a treated strength member element into a synthetic rope as outlined above, it is possible to monitor the general shape and geometry of a synthetic rope 1 using typical magnetic NDT devices.

In an example detection method, the synthetic rope with one or more treated strength member element(s) incorporated therein is scanned by a magnetic NDT device. For example, a magnetic flux leakage (MFL) device is used to scan the synthetic rope. The untreated strength member elements of the synthetic rope are not detectable by the MFL device. Therefore, the MFL device detects only the treated strength member element(s).

Figure 3:
FIG. 3 is a representative example of NDT output data according to one embodiment.

An example of output data of the MFL device used to monitor the synthetic rope with treated strength member element(s) is shown in FIG. 3. The output data obtained by detecting the treated strength member element(s) incorporated into the synthetic rope includes an amplitude 21 and a period 22. The amplitude 21 of the output data corresponds to a diameter of the synthetic rope at a given position along the synthetic rope. The period 22 of the output data corresponds to a lay length of the synthetic rope at a given position along the synthetic rope.

As the synthetic rope is used, its diameter typically decreases, and its lay-length typically increases due to the constant and/or repeated stresses to which the synthetic rope is subjected during use. This decrease in diameter and increase in the lay-length of the rope correspond to the deterioration of the synthetic rope's strength properties. Knowledge of these measurable attributes allows one to understand when the rope has experienced too much deterioration of the synthetic rope's strength properties. In other words, one may understand when the synthetic rope has sustained too much wear and/or damage to be safely used. Accordingly, one may also know when the synthetic rope 1, or a segment thereof, may need to be repaired or replaced.

For example, the synthetic rope may be subjected to too much wear or damage causing the diameter of the synthetic rope to decrease. The MFL device may output an amplitude 21 corresponding to the diameter of the synthetic rope based on the detection of treated strength member elements. When the amplitude 21 corresponding to the diameter of the synthetic rope 1 falls below a threshold value indicating that the rope has been subjected to too much damage, it may be determined that the synthetic rope 1, or a segment thereof, should be repaired or replaced.

Similarly, the synthetic rope may be subjected to too much wear or damage causing the lay-length of the synthetic rope to increase. The MFL device may output a period 22 corresponding to the lay-length of the synthetic rope based on the detection of treated strength member elements. When the period 22 corresponding to the lay length of the synthetic rope 1 exceeds a threshold value indicating that the rope has been subjected to too much damage, it may be determined that the synthetic rope 1, or a segment thereof, should be repaired or replaced.

The threshold values to determine when the synthetic rope, or a segment thereof, should be repaired or replaced are values which may be set by a user in advance. These values may be based on the known behavior of the treated and/or untreated strength member elements in the application in which the synthetic rope 1 is used. Further, the threshold values may be based on a localized diameter and lay-length, or an overall average diameter and lay-length of the synthetic rope.

For example, in the event of external damage to a portion of the synthetic rope, there would be localized elongation of the lay-length of the synthetic rope. Further, there would also be localized reduction in diameter of the synthetic rope. An MFL device would detect the treated strength member element(s) within the synthetic rope and output an amplitude 21 and period 22 corresponding to the localized lay-length elongation and diameter reduction. Accordingly, a user could determine that the synthetic rope, or the damaged segment of the synthetic rope, should be repaired or replaced.

Another example, in the event of repeated or constant stresses to the synthetic rope, the strength properties of the synthetic rope decrease over time. The decrease in strength properties corresponds to a reduced diameter and increased lay-length throughout the synthetic rope. An MFL device would detect the treated strength member element(s) within the synthetic rope and output an amplitude 21 and period 22 corresponding to lay-length elongation and diameter reduction throughout the synthetic rope. Accordingly, a user could determine that the synthetic rope should be repaired or replaced.

Further, as the synthetic rope is used and/or sustains damage, the condition of the treated strength member element(s) may degrade. Accordingly, the response detected by the MFL device may result in more noise or fluctuations in the data sets, including the existence of faults in the data. In this instance, a MFL device may be used to detect degraded or broken treated strength member elements along the length of the synthetic rope. The number and density of breaks in the treated strength member elements may be statistically correlated to the number of breaks of the strength member elements, and therefore correlated to retained strength of the synthetic rope. When the retained strength of the synthetic rope or a segment of the synthetic rope falls below a threshold based on the number of broken strength member elements, a user may determine that the synthetic rope, or segment thereof, should be repaired or replaced.

As can be appreciated from the foregoing, the use of the treated strength member elements in a rope as described herein permits multiple properties of the rope to be monitored, including changes in length and diameter, as well as breaks, as discussed above.

Further, it can be appreciated that the use of treated elements as described above may also be used to allow monitoring by NDT methods in cords, cables, belts, lines, and the like. For example, in one embodiment, a treated element may be incorporated into a fiber optic cable comprised of one or more optical transmission elements, for example glass based optical fibers, to allow monitoring of the fiber optic cable by NDT methods. For example, a treated element may be incorporated into a fiber optic cable in the same manner as detailed above for the synthetic rope, for example by including at least one treated element, such as a treated optical transmission element or other treated element detectable by an NDT device, into the fiber optic cable alongside the other optical transmission elements of the fiber optic cable, or an NDT detectable material may be would around a bundle of optical transmission elements of the fiber optic cable. Aspects of this embodiment are otherwise the same as discussed above for the synthetic rope, and thus the details of suitable treated elements for this embodiment are incorporated from above.

It will also be appreciated that any combination of the above described measurable attributes, or changes in the measurable attributes can be correlated to determine retained strength of the synthetic rope.

While the above evaluating method has been described with reference to an MFL device, it may be appreciated that other NDT methods may also be used. For example, an eddy current NDT device may similarly be used to detect measurable attributes of the treated strength member element(s) incorporated into the synthetic rope to evaluate the condition of the synthetic rope.

Evaluation of the synthetic rope by a method such as the above described NDT methods is desirably performed while the synthetic rope is still in use. For example, the synthetic rope is inspected by running rope past the evaluation device and/or by running the evaluation device along the synthetic rope without removing the synthetic rope from use. This is advantageous because it allows the synthetic rope to be evaluated without the time, labor, and expense associated with removing the synthetic rope for evaluation, and for similar costs associated with the down-time of the application in which the synthetic rope is used.

The above described synthetic rope and method for evaluating a synthetic rope may allow a synthetic rope to be applied in a number of critical applications where wire ropes may typically be used. Such applications include mining operations, drilling operations, use as mooring lines, tow lines, or winch lines, and other lifting and installation applications.

The synthetic rope may further be surrounded by a covering such as, for example, a mantle, jacket, sleeve, wrap, tape bonding, or polymer cover to protect the rope from environmental conditions or to provide mechanical protection to the rope.

What is claimed is:

1. A synthetic rope comprising:
synthetic material strength member elements, wherein at least one synthetic material strength member element is a treated strength member element, the treated strength member element renders the synthetic rope capable of being inspected by a magnetic or magnetic flux leakage non-destructive test (NDT) method, the at least one treated strength member element is a strength member fiber coated, clad and/or wrapped with a magnetically responsive material, the at least one treated strength member element comprises at least one synthetic fiber or non-metallic fiber with a magnetically responsive treatment, the at least one synthetic or non-metallic fiber are of a material chosen from the group consisting of: aramid, HMPE, PBO, LCP, polyamide, polyester, polyethylene, glass, and polypropylene, the synthetic rope further comprises untreated strength member elements that comprise synthetic or non-metallic fibers, and the synthetic or non-metallic fibers are of a material chosen from the group consisting of: aramid, HMPE, PEO, LCP, polyamide, polyester, polyethylene, glass, and polypropylene.

2. The synthetic rope according to claim 1, wherein the at least one treated strength member element is a strength member fiber coated or clad with a magnetically detectable material.

3. The synthetic rope according to claim 2, wherein the coating or cladding of the strength member element continuously covers an entire length of the strength member element.

4. The synthetic rope according to claim 3, wherein the strength member element is incorporated into the synthetic rope so as to run continuously along the entire length of the rope.

5. The synthetic rope according to claim 1, further comprising:
a first treated strength member element, or population of elements; and
a second treated strength member element, or population of elements, wherein
the first treated strength member element, has a stiffness less than untreated strength member elements, and
the second treated strength member element, has a stiffness equal to or higher than the untreated strength member elements.

6. A method comprising: treating a synthetic rope by coating or cladding at least one treated strength member element of me synthetic rope with a magnetically detectable material, and inspecting, using a magnetic based NDT device, the synthetic rope by means of the at least one treated strength member element detectable by the magnetic based NDT device, wherein the at least one treated strength member element comprises at least one treated synthetic or non-metallic fiber with a metallic coating or cladding, and wherein the at least one treated synthetic or non-metallic fiber with the coating or cladding are independently a material chosen from the group consisting of aramid, HMPE, PBO, LCP, polyamide, polyester, polyethylene, glass, and polypropylene, wherein the synthetic rope further comprises untreated strength member elements that comprise synthetic or non-metallic fibers, and wherein the synthetic or non-metallic fibers are of a material chosen from the group consisting of: aramid, HMPE, PEO, LCP, polyamide, polyester, polyethylene, glass, and polypropylene.

7. The method according to claim 6, wherein the method further comprises:
scanning the synthetic rope with the magnetic based NDT device; and
obtaining magnetic flux leakage or eddy current output data from the magnetic based NDT device;
wherein the output data relates to a condition of the synthetic rope.

8. The method according to claim 7, wherein the scanning is performed on the synthetic rope while the synthetic rope is in use.

9. The method according to claim 6, wherein the coating or cladding of the strength member element continuously covers an entire length of the strength member element.

10. The method according to claim 6, wherein the treated strength member element is incorporated into the synthetic rope so as to run continuously along the entire length of the rope.

11. The method according to claim 6, wherein
the synthetic rope incorporates a first treated strength member element or population of elements, a second treated strength member element or population of elements, and untreated strength member elements,
the first treated strength member element has a stiffness less than untreated strength member elements, and
the second treated strength member element has a stiffness equal to or higher than the untreated strength member elements.

12. The method according to claim 6, wherein, when the synthetic rope has multiple layers, directions, and/or patterns, the incorporating comprises incorporating at least one treated strength member element into each layer, direction, and/or pattern.

13. The method according to claim 7, wherein the obtained output data includes data corresponding to a localized diameter, a localized lay length, and a number and density of broken or degraded strength member elements of the synthetic rope.

14. The method according to claim 6, wherein, when the synthetic rope has an outer protective jacket, the at least one treated strength member element is incorporated into the outer protective jacket.

15. The method according to claim 6, wherein, when the synthetic rope has individual strand jackets, the at least one treated strength member element is incorporated into at least one of the strand jackets.

16. The synthetic rope according to claim 1, wherein the treated strength member element is formed integrally with at least one strand of the synthetic rope.

* * * * *